(12) United States Patent
Fabritius et al.

(10) Patent No.: US 7,368,603 B2
(45) Date of Patent: May 6, 2008

(54) METHOD FOR PURIFYING COMPOUNDS CONTAINING FUNCTIONAL GROUPS

(75) Inventors: Dirk Fabritius, Mainz (DE); Doreen Neumann, Hofheim (DE)

(73) Assignee: Lonza Ltd, Visp (CH)

( * ) Notice: Subject to any disclaimer, the term of this patent is extended or adjusted under 35 U.S.C. 154(b) by 430 days.

(21) Appl. No.: 10/807,062

(22) Filed: Mar. 23, 2004

(65) Prior Publication Data

US 2004/0192967 A1    Sep. 30, 2004

(30) Foreign Application Priority Data

Mar. 28, 2003   (DE)   ................ 103 14 078

(51) Int. Cl.
*C07C 51/42* (2006.01)
(52) U.S. Cl. ..................................... 562/608
(58) Field of Classification Search .............. 562/606; 560/248; 568/366, 410, 492, 699, 913
See application file for complete search history.

(56) References Cited

U.S. PATENT DOCUMENTS

| | | | |
|---|---|---|---|
| 3,922,217 A * | 11/1975 | Cohen et al. ............... | 208/299 |
| 5,959,128 A | 9/1999 | Kolstad et al. ............. | 554/206 |
| 6,025,384 A | 2/2000 | Cai et al. ..................... | 514/444 |
| 2004/0162437 A1* | 8/2004 | Fabritius et al. ............ | 554/191 |

FOREIGN PATENT DOCUMENTS

| | | |
|---|---|---|
| CS | 261464 | 1/1990 |
| JP | 61166399 | 7/1986 |
| JP | 61221298 | 10/1986 |
| JP | 09-268299 | 3/1998 |
| JP | 2001-354558 | 12/2001 |
| KR | 127510 | 12/1997 |
| WO | WO 02/098826 A2 | 12/2002 |

OTHER PUBLICATIONS

S. Nieto et al.: "Obtention of highly purified fractions of eicosapentaenoic acid and docosahexaenoic acid from sardine oil by silver-resin chromatography: A semi-preparative procedure" Grasasy Aceites, vol. 48, (1997) pp. 197-199.

* cited by examiner

*Primary Examiner*—Karl Puttlitz
(74) *Attorney, Agent, or Firm*—ProPat, L.L.C.

(57) ABSTRACT

The present invention relates to a method for producing a saturated organic compound bearing at least one functional group from a mixture which comprises this saturated organic compound containing at least one functional group and also one or more other organic compounds, which comprises
  i) mixing a silver-ion-loaded ion exchanger with the mixture at a temperature which is below the boiling point of the mixture,
  ii) then removing the supernatant and
  iii) detaching the ion-exchanger-bound, saturated organic compound having at least one functional group from the ion exchanger.

19 Claims, No Drawings

METHOD FOR PURIFYING COMPOUNDS CONTAINING FUNCTIONAL GROUPS

FIELD OF THE INVENTION

The invention relates to a method for producing a saturated organic compound bearing at least one functional group from a mixture which comprises this saturated organic compound containing at least one functional group and also one or more other organic compounds, which comprises
i) mixing a silver-ion-loaded ion exchanger with the mixture at a temperature which is below the boiling point of the mixture,
ii) then removing the supernatant and
iii) detaching the ion-exchanger-bound, saturated organic compound having at least one functional group from the cation exchanger using a solvent.

BACKGROUND OF THE INVENTION

Separating and purifying organic compounds from mixtures of substances is still, in many sectors, a problem which has not been solved satisfactorily. Removing certain impurities or separating mixtures of complex mixtures of substances requires specific methods. The success of the separation depends substantially on the structure of the compound to be removed; in particular for compounds of similar structure, specially adapted, frequently highly expensive, methods are required. Thus, for example, for partial esters of glycerol with higher fatty acids such as monoglycerides, scarcely any simple and effective methods are available for purification.

Monoglycerol esters, for example of oleic acid, palmitic acid, stearic acid, are the focus of economic interest. They have emulsifying, stabilizing, plasticizing and thickening properties and are used, for example, as emulsifiers for doughs, for sweeteners and baking aids, margarine and ice cream in the food industry (labeling for mono- and diglycerides of fatty acids: E 471). They are also used, for example, as lubricants in the plastics processing (for example: glycerol monostearate).

Reacting monoglycerides with acetic acid produces acetylated, liquid to waxy monoglycerides (acetoglycerides) which, owing to their good compatibility with active pharmaceutical compounds and their physiological safety, are used in foods as protective films, in cosmetics and pharmaceutical products.

Pharmaceutical applications particularly are increasingly becoming of public interest recently. For instance monoglycerides are described as PPAR activators (PPAR: Peroxisome Proliferator Activated Receptor) which are suitable for ameliorating overweight and diabetes (JP-A 2001-354558).

Monoglycerides are generally produced by transesterifying triglycerides with glycerol, or by reacting glycerol with corresponding fatty acids. However, the currently widespread lipase reaction (KR-A 127510, JP-A 09-268299) is also being used to synthesize monoglycerides and diglycerides. Usually, mixtures of triglycerides, diglycerides, monoglycerides, free fatty acids and glycerol are obtained, and in virtually all cases a purification is necessary, that is to say separation and enrichment of the monoglycerides from the complex mixtures.

Frequently distillation methods are used for this (Bornscheuer et al., Enzymes in Lipid Modification Ed. U. T. Bornscheuer, Wiley-VCH, 2000), which, however, owing to the high temperatures (T>200° C.) required in these methods, can only be used with restrictions, since acyl migrations or even the destruction of the desired products, in particular in the case of compounds sensitive to oxidation are the consequence (Naohiro et al. U.S. Pat. No. 6,025,384, Mares et al. CS-A 864520). This requires complex downstreaming to produce pure monoglycerides (Bornscheuer et al. see above).

A further current method for cleaning up is isolation via cold crystallization, since monoglycerides generally have different melting points from the corresponding tri-glycerides, diglycerides and free fatty acids. In some cases this successfully removes selectively the monoglycerides from diglycerides, triglycerides and other constituents.

However, this method is not universally usable, since non-uniform mixtures are difficult to work up, for example monoglycerides containing differing fatty acids, or monoglycerides which are present as regioisomers. The prochirality of many monoglycerides also plays a significant role. For instance, the melting points of rac-1-palmitoylglycerol (D,L-alpha-glycerol monopalmitate, approximately +74.9° C.) and 3-palmitoyl-sn-glycerol (L-alpha-glycerol monopalmitate, +71.1° C.) differ. The melting point of 2-monopalmitate (approximately +68° C.) is likewise different. The circumstance that the melting point is significantly affected by the fatty acid group makes selective crystallization difficult, in particular from mixtures.

In practice, the only separation which is successful is via crystallization of monoglycerides which bear fatty acids having more than 12 carbon atoms. Furthermore, the separation is considerably more difficult in the case of monoglycerides containing unsaturated fatty acids, for example oleic acid (18:1). In the case of polyunsaturated fatty acids the separation (crystallization) is virtually no longer successful.

Kang et al. (KR-A 94-6988) describe the synthetic preparation of monoglycerides and subsequent purification by means of solvent extraction.

Kolstad et al. describe a method for purifying monoglycerides by means of liquid-liquid extraction methods (U.S. Pat. No. 5,959,128).

Purification by column chromatography is described by Mekawa et al. (JP-A 61-166399). He successfully separates, in small yields, alpha- and beta-monoglycerides with the use of the ion-exchange material XAD, a synthetic-resin-based ion exchanger. Generally, the use of silica gels as ion-exchange material is not very suitable, since, owing to the acid behavior of many silica gels, an acyl migration can be catalyzed and thus purification opposed.

The PCT application 02/06158 describes an extraction method by selective complexation to a silver-ion-loaded cation exchanger and subsequent decomplexation to produce unsaturated, possibly derivatized, compounds from mixtures. This method is restricted to compounds containing highly unsaturated components, for example unsaturated long-chain fatty acids.

None of the known processes leads to satisfactory yields and sufficient selectivities in the purification of mixtures of compounds of the type described at the outset.

It is thus an object of the present invention to provide a method which permits the production of saturated organic compounds containing functional groups from mixtures which comprise these saturated organic compounds containing functional groups and also one or more other organic compounds. This method should make possible a quantitatively sufficient purification, a simplification of the method and an economic design of same. Furthermore, the method should be selective in order to make possible, for example, the separation of compounds which differ only slightly structurally.

BRIEF SUMMARY OF THE INVENTION

This object is achieved by a method for producing a saturated organic compound bearing at least one functional group from a mixture which comprises this saturated organic compound containing at least one functional group and also one or more other organic compounds, which comprises
  i) mixing a silver-ion-loaded ion exchanger with the mixture at a temperature which is below the boiling point of the mixture,
  ii) then removing the supernatant and
  iii) detaching the ion-exchanger-bound, saturated organic compound having at least one functional group from the cation exchanger using a solvent.

DETAILED DESCRIPTION OF THE INVENTION

A "saturated organic compound bearing at least one functional group" is taken to mean according to the invention a saturated organic compound which contains at least one group which is selected from =O, —OH, —C(O)OH, —C(O)H, —COOR, —C—O—C— and —C—O—R— (R=organic group). Preference is given to those compounds which bear active hydrogen atoms, such as carboxylic acids, hydroxycarboxylic acids, ketocarboxylic acids, alcohols, carboxylic esters, ethers and ketones. Examples of such compounds are long-chain, branched and unbranched, saturated alcohols having 12 to 30 carbon atoms, such as lauryl, myristyl, and stearyl alcohol and derivatives thereof, such as esters and ethers. Preference is likewise given to cyclic, saturated alcohols, for example stigmastanol, ergostanol, cholestanol and also stannols having further OH groups and/or different side chains (for example ethyl-branched, methyl-branched etc.).

Preference is likewise given to esters of hydroxycarboxylic acids, for example of glycolic acid, lactic acid, tartaric acid or hydroxybutyric acid, and also aminocarboxylic acids containing long-chain branched or unbranched saturated alcohols having 12 to 30 carbon atoms.

Further preferred compounds are derivatives (for example esters, ethers, adducts) of polyhydric alcohols, for example ethylene glycol, propylene glycol, propanediol, 1,2- or 1,3-butanediol; glycerol ethers with long-chain saturated alcohols, preferably fatty alcohols, or glycerol esters with long-chain saturated carboxylic acids, preferably fatty acids. Particular preference is given to mono- and diesters of glycerol with saturated fatty acids such as lauric, myristic, palmitic, palmitoleic, stearic, arachic and behenic acids, for example. Furthermore, preference is given to mono- and dialkyl ethers of glycerol, for example chimyl (=monoether of glycerol with a C16-alcohol) and batyl alcohol (=monoether of glycerol with a C18-alcohol).

The compounds to be separated according to the invention usually occur in mixtures with one or more organic compounds. These organic compounds can be, for example, structural isomers of the compounds to be enriched, mixtures of different classes of substance (for example ethers and esters) or mixtures of homologous series (for example esters which have bound differing fatty acids, for example C18 or C16), positional isomers or regioisomers.

A "silver-ion-loaded ion exchanger" is taken to mean a porous support, on the surface of which are situated silver ions. Expediently, the $Ag^+$ ion loading should be 100% of the theoretically possible loading. Since the maximum silver loading depends on the respective exchanger, it is not possible to give a capacity which is generally valid. The loading with a cation is usually reported in meq/g (meq=milliequivalent) or meq/ml wet (milliequivalents/milliliter wet weight). As an example, the maximum silver ion loading of an Amberlite 15 cation exchanger is 4.6 meq/g or 1.8 meq/ml.

Preferably, the porous supports are cation exchangers. Cation exchangers which can be used according to the invention are, in particular, those which have strongly acid properties. Gels which have styrene containing divinylbenzene branches as base, bear sulfonic acid and/or carboxyl groups as active silver-carrying group and are microporous or preferably macroporous are particularly preferred. In particular, macroreticular ion exchangers are also suitable, since they are solvent-stable and have a substantially higher surface area than gels. These macroreticular ion exchangers likewise bear sulfonic acid and/or carboxyl groups. Examples of such ion exchangers are: DOWEX® 50 WX8, DOWEX® 50 WX4, DOWEX® 50 WX2, DOWEX® MWC1, DOWEX® MSC1, DOWEX® Monosphere C-350, DOWEX® CCR-2, DOWEX® DR 2030, Amberlite® CG50, Amberlite® IR 120, AMBERLYST® 15, Bio-Rex® 70 Resin, Macherey & Nagel Ps-DVB®. Particular preference is given to AMBERLYST® 15 and DOWEX® DR 2030.

The silver-loaded ion exchangers are expediently produced on the basis of the method described by Nieto et al. (Nieto, S., A. M. Cordoba; J. Sanhuenzy and A. Valenzuela (1997): Obtention of highly purified fractions of eicosapentaenoic acid and docosahexaenoic acid from sardine oil by silver-resin chromatography: A semi-preparative procedure. Grasas y Aceites, 48(4), 197-199) for DOWEX® 50WX8 (earlier name DOWEX® W-HCR-W2). However, the method is simplified and modified. Neither is the support material prepared in a heatable glass column, nor is the support material prewashed with organic solvent. In the inventive method, in contrast to the method disclosed by Nieto et al., the particle size of the support material is critical for the quality of the separation and the yield. A relationship is exhibited between the amount of bound compound and the particle size of the material used. For instance, in the case of particle sizes greater than 50 mesh, addition of monoglycerides to a completely loaded (=100% load) cation exchanger is no longer found. Larger particles give somewhat poorer results (up to no binding at all, probably because of insufficient silver loading), smaller particle sizes, in contrast, do not give much better results, but in exchange have processing problems. Preference is given to particle sizes of from 20 to 50 mesh, preferably 100-400 mesh, very particular preference is given to 200-400 mesh, which ensure sufficient complexation.

The loading capacity of the ion exchangers which can be used according to the invention ranges from 0.1 to 15% by weight.

The selectivity can be controlled, depending on the compound to be separated. Generally the following applies. The more free p electrons (valences) a compound has, the more strongly it binds to the silver-loaded exchanger (complex bonding $Ag^+$ with the p electrons). The electron availability is also of importance here, that is to say the more accessible (not sterically hindered) the electrons are, the easier is the complex bonding. Aromatic compounds cannot be complexed as readily as linear olefins. The separation may likewise be controlled via the choice of solvent. The more polar the solvent, the complex bonding needs to be more strongly pronounced so that a compound is not detached from the exchanger. The strength is influenced firstly by the accessibility of the p electrons and secondly by the number of complex bonds. The more complex bonds, the stronger the interaction. Thus, monoglycerides, for example, may be separated from diglycerides, since monoglycerides permit enhanced complex bonding of the free p electrons of the oxygens from the alcohol group. The more nonpolar the solvent, the weaker the interaction can be for a compound still to interact with the exchanger. To detach the compounds, it is generally sufficient to use a solvent which is more polar than that which was used during binding. If appropriate, a higher temperature is employed in the same solvent. If the interaction should be too strong, detachment can be performed in any case using acetonitrile. The like applies to the temperature. The higher the temperature, the stronger must be the interaction for a compound to remain on the exchanger. In general, room temperature (approximately 26° C.) should be employed. Compounds can then be detached at temperatures below the boiling point of the solvent.

The properties of the ion exchanger are likewise of importance. For instance, macroreticular ion exchangers exhibit the best separation results in the case of hydrophobic compounds. This is particularly due to the porosity and the surface properties which have more exchanger groups on the surface than is the case with gel types. The more hydrophobic an exchanger, the better the binding of lipophilic compounds.

Time is likewise a variant which can be used to increase selectivity. In general, the shorter the binding time, the higher the purities of the compound primarily bound to the exchanger.

The water content in the cation exchanger likewise has a great influence on the activity of the cation exchanger. To obtain a high activity of the cation exchanger, it is expedient to keep the water content of the cation exchanger as low as possible, preferably less than 10 ppm, particularly preferably less than 5 ppm, in particular less than 3 ppm.

In the case of the inventive method, the following procedure is expediently followed: first, the mixture to be separated is dissolved in an organic solvent. Suitable solvents for binding the compound to the ion exchanger are, for example, alcohols, ketones, ethers, esters, diketones, diesters, diethers, diols, polyols, nitrites and dinitriles, preferably solvents permitted by law for food use such as hexane, ethanol, acetone or isopropanol, or a mixture of two or more of these solvents. Particular preference is given to methyl isobutyl ketone and ethanol.

The dissolved mixture of substances is then added to the ion exchanger. Expediently, a suspension is prepared of dissolved mixture of substances and ion exchanger. The suspension is then contacted with the ion exchanger at room temperature (approximately 26° C.) for from 0.5 to 5.0 hours, preferably from 1.0 to 3.5 hours, in particular from 1.2 to 1.7 hours. It has proved to be advantageous to stir or shake the suspension during this time. To reinforce the complexation process, it can be advantageous to supply heat to the suspension in order to achieve a higher purity of the complexed compound, that is to say to increase the selectivity of the method. Heating to from >40° C. to below the boiling point of the solvent used is advantageous. Preference is given to a temperature range of from 40 to 80° C.

It can further be advantageous to carry out the complexation process under a protective gas atmosphere, for example argon, to prevent unwanted reactions, for example with atmospheric oxygen or atmospheric moisture, which can lead to the deactivation of the ion exchanger and thus to insufficient complexation of the desired substance.

The compound bound to the ion exchanger can then, after the supernatant is decanted off, be separated from the ion exchanger and thus isolated. Expediently, this is performed using a suitable solvent. Solvents which can be used for detaching the compound from the ion exchanger are alcohols, preferably ethanol, ethers, ketones, esters, nitriles or a mixture of such solvents. Generally, during binding, a colder solvent is used than during detachment. Expediently, a more nonpolar solvent is used during binding than during detachment. An ideal solvent for detachment is acetonitrile, but this has the disadvantage that it is toxic. Particular preference is given to ethanol (hot for binding and cold for detachment). A suitable solvent for binding is likewise, preferably, hexane.

Alternatively, the "unwanted" compound can be bound selectively to the ion exchanger, in which case the wanted compound then accumulates in the supernatant and can be isolated there. The variant of the inventive method which is preferred depends on the type, number and position of the functional group. Generally, the more polar compound binds to the exchanger and the more nonpolar compound remains in the supernatant. However, the accessibility of the functional group is also important, as 1-monoglycerides bind markedly better to the exchanger than 2-monoglycerides, since there the two remaining OH groups are shielded by the fatty acid group. Thus, for example, triglycerides containing saturated fatty acids can be separated simply from monoglycerides containing a saturated fatty acid, since the triglycerides do not bind to the exchanger.

Using the inventive method, compounds may be concentrated in high purities and yields from complex mixtures of substances by simple binding to an ion exchanger. In contrast to chromatographic methods in which separation is only achieved after a certain number of plates or after, in some circumstances, a very high number of equilibria is established, in the inventive method only a single equilibrium is established during the complexation process. Technical problems which usually occur owing to change of solvent in the chromatography (air bubbles, sources of the exchanger, inhomogeneities, etc.) do not occur in the inventive method. Likewise, flow problems (inhomogeneous flow) do not occur over the separation column (gradient formation). High product purities can be achieved simply using the inventive method.

In a simple manner, particularly preferably, mixtures of monoglycerides and diglycerides (for example 1:1 mixture of 1,2- and 1,3-dipalmitate) may be purified.

It is particularly surprising that the method is likewise outstandingly suitable for mixtures consisting of monoglycerides containing fatty acids substituted at different positions. Thus, for example, a mixture of 1-monomyristate and 2-monopalmitate may be separated in a simple manner by selective binding of 1-monomyristate to the cation exchanger.

The inventive method is an enormous simplification and economic improvement of the purification methods described in the prior art.

The invention will be described in more detail on the basis of examples hereinafter. In the examples the following measurement methods were used:

Gas-chromatographic Analysis

The oils are analyzed following transesterification by generally known methods (for example methanolic hydrochloric acid) to the methyl esters and subsequent gas-chromatographic analysis (Hewlett-Packard GC6890, column: Macherey & Nagel FFAP Permabond 0.1 μm (25 m, 0.25 mm), split mode (10:1), carrier gas: helium (constant flow 1.0 ml/min), FID operated using hydrogen (30 ml/min) and oxygen (300 ml/min) as fuel gases, makeup: 20 ml of helium, detector and injector temperature: in each case 225° C., GC oven temperature program: start temperature 160° C., holding phase 12 minutes isothermal, temperature rise rate 10° C./min to final temperature 230° C., hold this for 5 min, injection volume; 1.0 ml). By adding an internal standard (for example a saturated fatty acid methyl ester such as methyl heptadecanoate [C17] (this does not bind)) to the reaction batch, quantitative analysis can be carried out; results are reported in area %.

Preparation of AMBERLYST® 15 (20-50 Mesh) Loaded Up to 100% with Silver Ions 20 g of AMBERLYST® 15 are placed in a vacuum filter or glass column equipped with a vacuum filter and washed with 1 M sodium nitrate solution (NaNO$_3$) until the pH of the eluate changes from acid to neutral. Neutralization indicates decreased formation of nitric acid which is formed on exchange of protons for sodium ions. When the cation exchanger is completely loaded with sodium ions, the eluate remains neutral.

Then two different procedures can be followed. Either, the sodium-ion-loaded cation exchanger is washed with 0.4 M silver nitrate solution until silver ions are detectable in the eluate, or the cation exchanger is first transferred to a round-bottom or conical flask using sodium nitrate solution. The excess sodium nitrate solution is then discarded. The cation exchanger is then stirred with 5.4 ml of 0.4 M silver nitrate solution/g of AMBERLYST® 15 for 8-12 h. The supernatant is discarded.

The cation exchanger (approximately 2.0 mmol of Ag$^+$/ml of H$^+$ exchanger with 1 g of H$^+$ DOWEX approximately corresponding to 0.9 ml of H$^+$ of DOWEX) is washed three times with 100 ml of water to be free of silver ions and is then washed twice with 100 ml of ethanol to be free of water; for this the batch is stirred for 1 hour. Then, the cation exchanger is allowed to stand overnight (12 h) in 100 ml of acetonitrile. Thereafter it is again washed twice each time with 100 ml of ethanol. The ion exchanger can then be used. Acetonitrile can alternatively be replaced by using three times 100 ml of ethanol.

EXAMPLE 1

Separation of a Mixture of 1-monomyristate and a 1,2/1,3-dipalmitate Mixture

Since the analysis of fatty acids generally proceeds relatively simply and quickly, in this example the selectivity of the exchanger with respect to binding of monoglycerides and diglycerides containing various fatty acids was put to use. In this manner it was possible to identify relatively rapidly whether monoglycerides (MG) or diglycerides (DG) are bound preferentially.

181.2 mg of 1-monomyristate (Sigma-Aldrich) and 173.1 mg of dipalmitate mixture (1:1 mixture of 1,2-DG and 1,3-DG, Sigma-Aldrich) are dissolved in 120 ml of methyl isobutyl ketone and added to 52.1 g of fully silver-loaded AMBERLYST® 15 ion exchanger. Analysis of the starting mixture shows a myristic acid content of 47.0% by weight and a palmitic acid content of 53.0% by weight. The mixture is shaken in a conical flask for 90 minutes at room temperature (26° C.) at 100 rpm.

The supernatant is then taken off and the exchanger is washed three times with 50 ml of methyl isobutyl ketone. The combined solvent extracts are concentrated on a rotary evaporator. This produces 265.0 mg of a solid white residue. GC analysis shows a myristic acid content of 37.6% by weight and a palmitic acid content of 62.4% by weight.

The exchanger is washed three times, each time with 100 ml of ethanol for one hour. The supernatants are combined and likewise concentrated. 101.2 mg of a white solid product are isolated. GC analysis after transesterification of the two fractions (supernatant methyl isobutyl ketone and ethanol wash fraction) gives the following picture:

The product fraction shows a myristic acid purity of 76% by weight, and that of palmitic acid 24.4% by weight. It may be seen that the bound material is predominantly 1-monomyristate, since myristic acid is detected virtually exclusively.

TABLE 1

| | 1-Monomyristate 181.2 mg | 1,2- and 1,3-dipalmitate (1:1 mixture) 173.1 mg | Total |
|---|---|---|---|
| GC analysis (area-%) | 47.0% | 53.0% | |
| Supernatant GC analysis (area-%) | 37.6% | 62.4% | 265.0 mg |
| AMBERLYST* GC analysis (area-%) | 76.0% | 24.4% | 101.2 mg |

*after elution from the ion exchanger

EXAMPLE 2

Separation of a Mixture of 1-monostearate and 2-monopalmitate 50.0 mg of 2-monopalmitate (Sigma-Aldrich) and 51.0 mg of 1-monostearate (Sigma-Aldrich) are dissolved in 100 ml of methyl isobutyl ketone and added to 10 g of fully silver-loaded AMBERLYST® 15 ion exchanger. Analysis of the starting mixture shows a stearic acid content of 48.0% by weight and a palmitic acid content of 51.2% by weight. The suspension is shaken for 90 minutes at room temperature (26° C.) at 100 rpm in the conical flask.

The supernatant is then taken off and the exchanger is washed five times with 100 ml of methyl isobutyl ketone. The combined solvent extracts are concentrated on the rotary evaporator. This produces 61.6 mg of a solid white residue. GC analysis shows a palmitic acid content of 47.2% by weight and a stearic acid content of 46.6% by weight.

The exchanger is washed three times, each time with 100 ml of ethanol for one hour. The supernatants are combined and likewise concentrated. 49.2 mg of a white solid product are isolated. GC analysis after transesterification of the two fractions (supernatant methyl isobutyl ketone and ethanol washing fraction) gives the following picture:

The product fraction shows a purity of stearic acid of 57.5% by weight and of palmitic acid of 36.2% by weight. It may be seen that the bound material is enriched 1-monostearate, since chiefly stearic acid was detected.

TABLE 2

|  | 1-Monostearate 51.0 mg | 2-Monopalmitate 50.0 mg | Total |
| --- | --- | --- | --- |
| GC analysis (area-%) | 48.0% | 51.2% |  |
| Supernatant |  |  | 61.6 mg |
| GC analysis (area-%) | 46.6% | 47.2% |  |
| AMBERLYST* |  |  | 49.2 mg |
| GC analysis (area-%) | 57.5% | 36.2% |  |

*after elution from the ion exchanger

If the ratio of 1-monostearate to 2-monopalmitate used is changed from 5.1:4.8 to 4.5:5.4, product fractions can be isolated which have a stearic acid content greater than 70%.

The invention claimed is:

1. A method for separating a saturated organic compound bearing at least one functional group from a mixture which comprises this saturated organic compound containing at least one functional group and also one or more other organic compounds, which comprises
   i) mixing a silver-ion-loaded ion exchanger with the mixture at a temperature which is below the boiling point of the mixture,
   ii) then removing the supernatant and
   iii) detaching the ion-exchanger-bound, saturated organic compound having at least one functional group from the ion exchanger,
   wherein the saturated organic compound containing at least one functional group which is bound to the ion exchanger is detached from the ion exchanger using a solvent; the saturated organic compound bearing a functional group contains at least one group which is selected from =O, —OH, —C(O)OH, —C(O)H, —COOR, —C—O—C— and —C—O—R—, where R is an organic group, and the ion exchanger has a water content of less than 10 ppm.

2. The method as claimed in claim 1, wherein the saturated organic compound bearing a functional group bears at least one active hydrogen atom.

3. The method as claimed in claim 1, wherein the saturated organic compound bearing a functional group is selected from the group consisting of carboxylic acids, hydroxycarboxylic acids, ketocarboxylic acids, alcohols, carboxylic esters, ethers and ketones.

4. The method as claimed in claim 1, wherein the saturated organic compound bearing a functional group is selected from the group consisting of: alcohols having from 12 to 30 carbon atoms, esters of hydroxycarboxylic acids and/or aminocarboxylic acids and esters or ethers of polyhydric alcohols.

5. The method as claimed in claim 4, wherein the saturated organic compound bearing a functional group is selected from the group consisting of: esters or ethers of ethylene glycol, propylene glycol, propanediol, 1,2- or 1,3- butanediol and glycerol.

6. The method for separating a saturated organic compound bearing at least one functional group from a mixture which comprises this saturated organic compound containing at least one functional group and also one or more other organic compounds, which comprises
   i) mixing a silver-ion-loaded ion exchanger with the mixture at a temperature which is below the boiling point of the mixture,
   ii) then removing the supernatant and
   iii) detaching the ion-exchanger-bound, saturated organic compound having at least one functional group from the ion exchanger,
   wherein the saturated organic compound bearing a functional group is selected from the group consisting of chinyl, batyl and selachyl alcohol, and the ion exchanger has a water content of less than 10 ppm.

7. The method as claimed in claim 5, wherein the saturated organic compound bearing a functional group is selected from the group consisting of mono- and disubstituted glycerol, the substituents being identical or different fatty acids.

8. The method as claimed in claim 1, wherein the ion exchanger is a cation exchanger.

9. The method as claimed in claim 1, wherein the ion exchanger has acid properties and is microporous, macroporous or macroreticular.

10. The method as claimed in claim 9, wherein the cation exchanger is macroreticular.

11. The method as claimed in claim 10, wherein the macroreticular cation exchanger comprises at least one of either sulfonic acid or carboxyl groups.

12. The method as claimed in claim 1, wherein the solvent is selected from the group consisting of alcohols, ethers, ketones, esters, nitriles and mixtures of two or more of these solvents.

13. The method as claimed in claim 12, wherein the solvent is ethanol.

14. The method as claimed in claim 1, wherein the mixture is dissolved in a solvent which is selected from one or more compounds of the group consisting of alkanes, ketones, ethers, esters, diketones, diesters, diethers, diols, polyols, nitriles, dinitriles and alcohols.

15. The method as claimed in claim 1, wherein said saturated organic compound containing at least one functional group has greater polarity and/or less stork hindrance than the one or more organic compounds.

16. The method as claimed in claim 1, wherein the saturated organic compound bearing a functional group is selected from the group consisting of laurie, myristic, palmitic, palmitoleic, stearic, arachic and behenic acids.

17. The method as claimed in claim 1, wherein the silver-ion-loaded ion exchanger has a particle size of from 20 to 50 mesh.

18. The method as claimed in claim 1, wherein said mixture is a mixture of ethers and esters, a mixture of a homologous series, a mixture of positional isomers or a mixture of regioisomers.

19. The method as claimed in claim 1, wherein said mixture is a mixture of esters bound to differing fatty acids.

* * * * *

UNITED STATES PATENT AND TRADEMARK OFFICE
CERTIFICATE OF CORRECTION

PATENT NO. : 7,368,603 B2 Page 1 of 1
APPLICATION NO. : 10/807062
DATED : May 6, 2008
INVENTOR(S) : Fabritius et al.

It is certified that error appears in the above-identified patent and that said Letters Patent is hereby corrected as shown below:

Claims

Column 10
Claim 6, Line 13, delete "chinyl" insert --chimyl--
Claim 15, Line 43, delete "stork" insert --steric--
Claim 16, Line 47, delete "laurie" insert --lauric--

Signed and Sealed this

Eighth Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 7,368,603 B2  
APPLICATION NO. : 10/807062  
DATED : May 6, 2008  
INVENTOR(S) : Fabritius et al.

Page 1 of 1

It is certified that error appears in the above-identified patent and that said Letters Patent is hereby corrected as shown below:

Claims

Column 10  
Claim 6, Line 13, delete "chinyl" insert --chimyl--  
Claim 15, Line 43, delete "stork" insert --steric--  
Claim 16, Line 47, delete "laurie" insert --lauric--

Signed and Sealed this

Twenty-second Day of July, 2008

JON W. DUDAS  
*Director of the United States Patent and Trademark Office*